US007324195B2

(12) United States Patent
Packirisamy et al.

(10) Patent No.: US 7,324,195 B2
(45) Date of Patent: Jan. 29, 2008

(54) PLANAR WAVEGUIDE BASED GRATING DEVICE AND SPECTROMETER FOR SPECIES-SPECIFIC WAVELENGTH DETECTION

(75) Inventors: Muthukumaran Packirisamy, Dorval (CA); Ashok Balakrishnan, Ottawa (CA)

(73) Assignee: Valorbec Societe Em Commandite, Montreal, Quebec (CA)

( * ) Notice: Subject to any disclaimer, the term of this patent is extended or adjusted under 35 U.S.C. 154(b) by 187 days.

(21) Appl. No.: 11/031,039

(22) Filed: Jan. 10, 2005

(65) Prior Publication Data

US 2005/0151966 A1  Jul. 14, 2005

Related U.S. Application Data

(60) Provisional application No. 60/534,696, filed on Jan. 8, 2004.

(51) Int. Cl.
*G01J 3/28* (2006.01)
*G01J 3/30* (2006.01)
*G02B 6/10* (2006.01)
*G02B 6/00* (2006.01)
*G02B 6/12* (2006.01)
*G01N 1/10* (2006.01)

(52) U.S. Cl. ............... 356/328; 356/317; 356/246; 385/131; 385/132; 385/12; 385/14

(58) Field of Classification Search ............ 356/328, 356/246, 410, 411, 317; 385/129–132, 12, 385/14
See application file for complete search history.

(56) References Cited

U.S. PATENT DOCUMENTS 4,571,024 A * 2/1986 Husbands .................. 385/37

| 5,228,103 | A  | * | 7/1993  | Chen et al. ............... 385/14  |
| 5,351,262 | A  | * | 9/1994  | Poguntke et al. ......... 372/102  |
| 5,937,113 | A  | * | 8/1999  | He et al. ................... 385/11 |
| 5,966,483 | A  | * | 10/1999 | Chowdhury ............... 385/37   |
| 5,991,023 | A  | * | 11/1999 | Morawski et al. ......... 356/326 |
| 6,002,479 | A  | * | 12/1999 | Barwicz et al. ........... 356/326 |
| 6,097,863 | A  | * | 8/2000  | Chowdhury ............... 385/37   |
| 6,438,279 | B1 | * | 8/2002  | Craighead et al. ......... 385/12 |
| 6,563,977 | B1 | * | 5/2003  | Chen et al. ............... 385/24 |

(Continued)

OTHER PUBLICATIONS

J. Mohr, B. Anderer, and W. Ehrfeld, "Fabrication of a Planar Grating Spectrograph by Deep-etch Lithography with Synchrotron Radiation", 1991, Sensors and Actuators A: Physical, v.25-27, p. 571-575.*

(Continued)

*Primary Examiner*—Gregory J Toatley, Jr.
*Assistant Examiner*—Bryan J Giglio (57) ABSTRACT

Planar waveguide based grating devices and spectrometers, for species-specific wavelength detection for example, are disclosed. A planar waveguide spectrometer apparatus may have a microfluidic channel or compartment microfabricated integrally with a planar waveguide or hybrid assembled with the planar waveguide and optically coupled thereto. The planar waveguide may also include a thin planar substrate which is made of a transparent waveguiding optical material and has a planar multilayer, one or more input waveguides, a waveguide-based spectrometer, and one or more output waveguides integrally formed thereon. An apparatus which incorporates a planar waveguide, a diffractive construct for diffracting light through the planar waveguide onto a curved image surface, and a plurality of output waveguides emanating from the curved image surface at locations selected to extract predetermined wavelengths or wavelength ranges, is also disclosed.

13 Claims, 6 Drawing Sheets

U.S. PATENT DOCUMENTS

| | | | | |
|---|---|---|---|---|
| 6,657,723 | B2* | 12/2003 | Cohen et al. | 356/328 |
| 6,766,077 | B2* | 7/2004 | Packirisamy et al. | 385/37 |
| 6,959,138 | B2* | 10/2005 | Steenblik et al. | 385/131 |
| 2002/0072243 | A1* | 6/2002 | Craighead et al. | 438/745 |
| 2004/0240063 | A1* | 12/2004 | Delage et al. | 359/571 |
| 2005/0088648 | A1* | 4/2005 | Grace et al. | 356/318 |
| 2005/0219701 | A1* | 10/2005 | Balakrishnan et al. | 359/572 |

OTHER PUBLICATIONS

State-of-the-Art in Integrated Optical Microspectrometers, R.F. Wolffenbuttel, Feb. 2004, IEEE Transactions on Instrumentation and Measurement, v.53, n.1.*

Selffocussing phase transmission grating for an integraed optical microspectrometer, D. Sander & J. Muller, 2001, Sensors and Actuators A, v.88, n.1-9.*

Xingyong, Wu., et. al., Immunofluorescent Labeling of Cancer Marker Her2 and Other Cellular Targets with Semiconductor Quantum Dots, Nature Biotechnology vol. 21, Jan. 2003, pp. 41-46.

Ian Kennedy, "Application of Quantum Dots to Environmental and Cell Biology", NSF Nanoscale Science and Engineering Grantees Conf., Dec. 11-13, 2002.

Mark L. Adams, "Microfluidic Integration on Detector Arrays for Absorption and Fluorescence Micro-spectrometers", Sensors and Actuators A, 104, 2003, pp. 25-31.

Emilio Gini, et. al., "Polarization Independent InP WDM Multiplexer/Demultiplexer Module", Jrl. of Lightwave Technology, vol. 16, No. 4, Apr. 1998, pp. 625-630.

"High Quality—Production Quantities of Core Semiconductor Nanocrystals for the Nanotechnology Researcher", Evident Technologies, Aug. 2002.

K.A.McGreer, "Flat Field Grating Demultiplexer for WDM", Canadian Journal of Physics, 74, 1996, p. S25-S28.

K.A.McGreer, "A Flat Field Broadband Spectrograph Design", IEEE Photonics Technology Letters, vol. 7, No. 4, Apr. 1995, pp. 397-399.

* cited by examiner

PLANAR WAVEGUIDE BASED GRATING DEVICE AND SPECTROMETER FOR SPECIES-SPECIFIC WAVELENGTH DETECTION

CROSS-REFERENCE TO RELATED APPLICATION

This application claims the benefit of U.S. Provisional Patent Application Ser. No. 60/534,696, filed on Jan. 8, 2004, entitled "PLANAR WAVEGUIDE BASED GRATING DEVICE AND SPECTROMETER FOR SPECIES-SPECIFIC WAVELENGTH DETECTION", and incorporated in its entirety herein by reference.

FIELD OF THE INVENTION

This invention relates generally to spectroscopy and, in particular, to planar waveguide based grating devices therefor.

BACKGROUND

The miniaturization and integration of spectrographic equipment, using MEMS (Micro Electromechanical Systems) devices, for example, draw great attention for the potential application of spectrographic techniques to different fields of technology. Wavelength signature detection, for example, has immense potential for application in such fields as telecommunications, biological sensing, chemical sensing, and sensing of other material properties that respond through spectral variation of light. Chemical and biological sensing and diagnostics have a tremendous potential for applications in many fields including defence, medicine, space, aerospace, etc.

However, widespread application of known detection techniques has been hampered by the typically large size and high cost of equipment. According to conventional design techniques, equipment is not application-specific, and is instead adapted for many different uses. For example, different chemical or biological species have different combinations of wavelength signature or peak wavelengths for detection. Hence, using a general wavelength detection equipment for the detection of different species becomes highly demanding due to the wider range of wavelength and finer wavelength resolution required in such applications.

In a spectrometer, all signature wavelengths are generally imaged on a detector array with constant array spacing, such that a large number of detector array elements is required in order to cover a full wavelength range of interest, leading to increased equipment costs. Furthermore, in the detection of specific chemicals or biological specimens with a characteristic spectrum over a wide wavelength range, not all wavelengths, and therefore not all elements in a large detector array, are needed. This results in unused detector elements corresponding to non-excited wavelengths.

Known wavelength detection equipment is also characterized by relatively large required sample quantities, as well as long light paths between the sample and a detection unit, which affects equipment size.

SUMMARY OF THE INVENTION

According to one broad aspect, the invention provides a planar waveguide spectrometer apparatus having a microfluidic channel or compartment microfabricated integrally with a planar waveguide or hybrid assembled with the planar waveguide and optically coupled thereto.

In one embodiment, the planar waveguide includes a thin planar substrate made of a transparent waveguiding optical material. A planar multilayer, one or more input waveguides, a waveguide-based spectrometer, and one or more output waveguides are integrally formed on the thin planar substrate. The planar multilayer has differing refractive indices to allow guiding of light in a direction disallowing diffusion of light perpendicular to the plane of the layers. The waveguides further guide light radiation within each structure transversely from an input edge of the substrate disallowing diffusion of radiation in a direction along the multilayer plane and parallel to the input edge, said input waveguides to guide light a predetermined distance to a termination edge or image line. The waveguide-based spectrometer has diffractive elements and slab regions between the input waveguides, the diffractive elements and output waveguides, with an input region coincident to the termination edges of the input waveguides, the diffractive elements being adapted to separate a plurality of input wavelengths into separate focal spots along an image plane of desired curvature perpendicular to the optical guiding multilayer. The output waveguides are similar to the input waveguides, begin at the image plane of the spectrometer at positions suitable for capturing radiation at desired wavelengths, and guide the radiation to an output edge perpendicular to the optical multilayer planes and coincident with an output plane of the termination of the output waveguides. A detector array is placed facing the output edge with detector elements following all or some of the output waveguides at their termination points. In this case, the microfluidic channel or compartment is microfabricated integrally with the thin planar substrate or hybrid assembled with the thin planar substrate and optically coupled thereto.

The planar multilayer may include at least two layers, with one layer, a guiding layer or core layer, in the midst of all layers having a refractive index exceeding the indices of adjacent layers.

Structures which give transverse definition to the input and output waveguides may include a pair of walls perpendicular to the plane of the optical layers, cutting through at least the guiding layer, and surrounded on either side by optical material of lower index than that of the guiding layer.

The spectrometer may include a planar waveguide at both the input edge and the image plane, said planar waveguide extending to a reflective diffraction grating with grating facets constructed perpendicular to the guiding layer and intersecting the guiding layer. In some embodiments, the image plane is curved, with radius R, lying on a Rowland circle, and the centers of the grating facets lie in a curved plane of radius twice R.

An optical fiber may be aligned to an input waveguide at the input edge to deliver radiation at a plurality of wavelengths within a predetermined spectral range.

The apparatus may also include an electronic subsystem for collecting signals from the array for processing and correlation, and allowing the processed signal to be interpreted for information about a system being studied using the radiation incident to the input edge of the device.

In some embodiments, multiple diffraction orders from the spectrometer are allowed to illuminate the output waveguides, and unwanted orders are eliminated on a waveguide-by-waveguide basis by means of lithographically defined scattering from resonant perturbations of the output waveguides or by filters added to the output waveguide paths.

Desired wavelengths captured by the output waveguides may be either equispaced for continuous mapping or non-equispaced for the selective mapping of wavelengths.

The apparatus may be optimized for detection of fluorescence from quantum dot fluorescent tags or fluorescent dyes.

In some embodiments, the microfluidic channel or compartment includes a fluorescence chamber coupled to the planar waveguide via high numerical-aperture optics. The fluorescence chamber is either integrated with the planar waveguide either by means of passive alignment therewith or integrated monolithically with the planar waveguide, and may be designed as a standard microfluidics system, employing electro-osmotic flow or pressure induced flow.

Uses of the apparatus may include, for example, DNA sequencing, bio imaging or other applications through wavelength detection of fluorescent markers, fluorescent dyes and quantum dots.

According to another broad aspect, the invention provides an apparatus comprising a planar waveguide, a diffractive construct for diffracting light through the planar waveguide onto a curved image surface, and a plurality of output waveguides emanating from the curved image surface at locations selected to extract predetermined wavelengths or wavelength ranges. The diffractive construct may be a diffraction grating, for instance.

In some embodiments, the planar waveguide, the diffractive construct, and the plurality of output waveguides are integrated on a single multi-layer structure, at least one layer of which is a waveguiding layer at least between the diffractive construct and the curved image surface and in the output waveguides. The at least one layer preferably has a higher index of refraction than adjacent layers between the diffractive construct and the curved image surface, and in the output waveguides.

In some embodiments, the curved image surface is a Rowland circle, and the diffractive construct is a curved diffraction grating. For example, the curved surface may have a radius one half a radius of the Rowland circle.

The apparatus may also include at least one input waveguide for directing input light towards the diffractive construct.

A detector element for each of at least some of the output waveguides is also preferably provided.

Other aspects and features of the present invention will become apparent, to those ordinarily skilled in the art, upon review of the following description of the specific embodiments of the invention.

BRIEF DESCRIPTION OF THE DRAWINGS

The invention will now be described in greater detail with reference to the accompanying diagrams, in which.

DETAILED DESCRIPTION OF THE PREFERRED EMBODIMENTS

Figure 1:
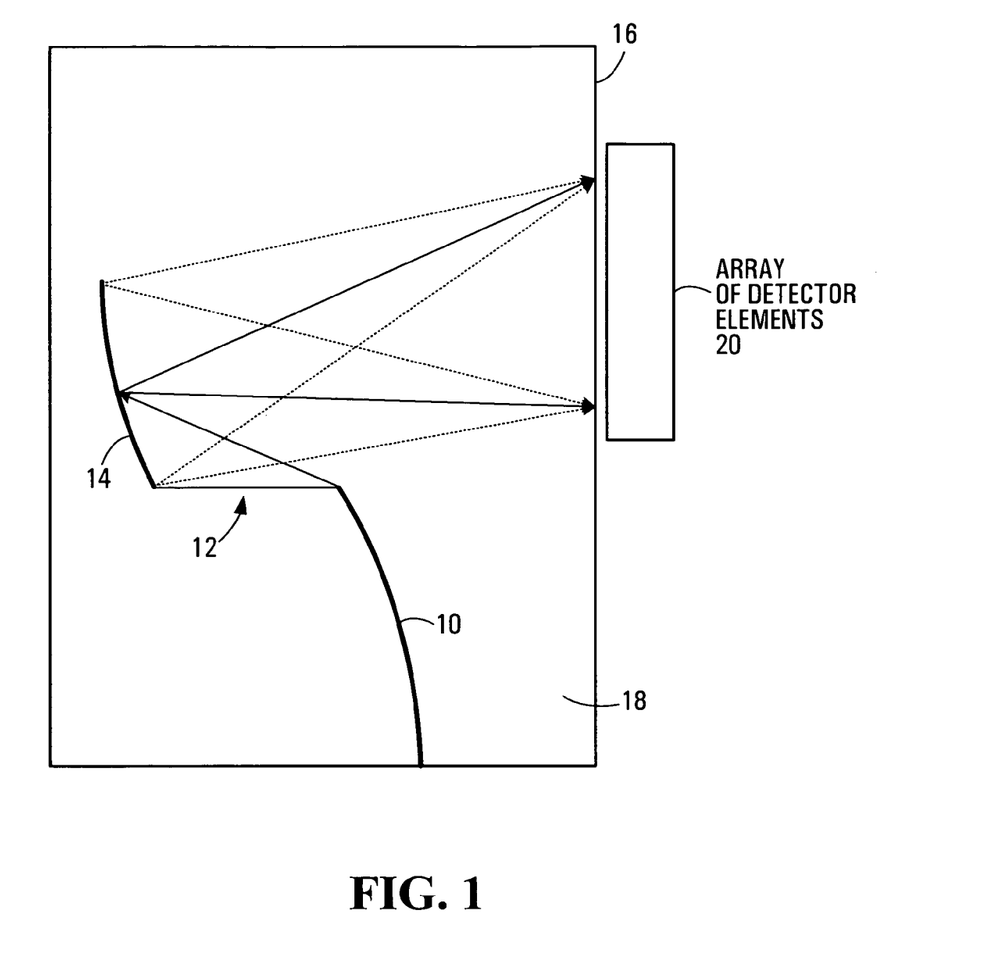
FIG. 1 is a diagram of a known waveguide based spectrometer.

FIG. 1 is a diagram of a known waveguide based spectrometer. As shown, the spectrometer comprises an input waveguide 10, a slab or planar waveguide section 12, and a diffractive construct 14, fabricated on a thin planar optical substrate 18. An array 20 of detecting elements is adjacent, and typically attached, to an edge 16 of the substrate 18.

The waveguide based spectrometer shown in FIG. 1 is adapted for equally spaced wavelengths. Light is guided along the input waveguide 10, where it enters the slab waveguide section 12, allowing the light to spread out and cover the diffractive construct 14. The diffractive construct 14 may, for example, be an Echelle grating or the phase-delayed waveguide array of an AWG (Arrayed Waveguide Grating) device. The diffractive construct 14 separates different wavelengths into different positions along an image line at the edge 16.

The image line produced by the diffractive construct in FIG. 1 is a substantially straight line, as shown, along the edge 16 of the substrate 18. The array 20 of detector elements typically attaches to the edge 16 of the substrate 18 in order to obtain a spectrum. For most focusing spectrometer designs, a straight image line is not the ideal image line. In fact, the best images, and therefore the highest quality factor spectra, are obtained when the grating or diffractive construct 14 is tangent to a Rowland circle, the image line lies on the Rowland circle, and the grating itself is approximately twice the radius of the Rowland circle. In the case of an Echelle grating design, generalized 2-point astigmatic design can be used in order to improve the quality factor of the spectra beyond that obtained by the pure Rowland circle geometry. See [6] and [7] for example.

In addition, if the portions of a spectrum that are of interest in a particular application are widely separated in wavelength, and a spectrometer is consistently used to detect material with that specific spectrum, there is a wide region of the output that is not of use for that particular application. However, as described above, known detector arrays invariably have detector elements throughout the active physical range, and as such include unused detector elements.

In accordance with an aspect of the invention, a spectrometer is constructed on a waveguide material substrate with the flexibility of optimising the quality factor through selective diffraction. Different wavelengths of diffracted light from a grating element are guided through suitable waveguides from an image line to optical detectors at an edge of the optical chip, comprising the substrate as well as diffractive and waveguiding structures fabricated thereon, with the possibility of either continuous or selective mapping. In either form of mapping, the waveguides terminate at the edge of the chip in line with detector elements, regardless of the spectrometer wavelength dispersion at the image line. In both cases, the pitch or separation between the waveguides at the chip edge is determined by the pitch between the detector elements.

Positioning of waveguides for continuous mapping corresponds to equi-spaced wavelengths covering a selected range of spectrum. For selective mapping, such as in a species detection application for instance, waveguide positions correspond to a selected set of wavelengths that characterize the species in detection.

In a preferred embodiment of the invention, a spectrometer comprises an optical chip integrating a waveguide and a grating element as a diffractive construct. In order to allow wavelength selectivity, the diffractive construct is designed to have an image surface which is curved and perpendicular to the waveguide. In a so-called Rowland circle design, the waveguide would point towards the center of the grating of radius 2R, and the ends of the guide would lie on an image line of radius R tangent to the grating at its center. The core, light guiding region of the slab is defined between the diffractive construct and the curved image surface. By including additional waveguides which carry light away from the curved image surface at selected locations, wavelength selectivity is achieved. Each such waveguide is provided with a respective detector element (s).

Fluorescence labeling using fluorescent markers, fluorescent dyes and quantum dots are standard practice in many biological, medical applications including DNA sequencing, bio imaging, color filtering, etc. Even though the present invention can be applied to all of the above methods, application with quantum dots are give in this patent as only an example of the invention. Presently the labeling is accomplished by fluorescent dyes. In future such labeling might be accomplished with quantum dots. A quantum dot [5] is a crystalline material with small (nanometer-scale) size. The small size modifies the optical properties of the crystal, allowing a controllable absorption and fluorescence spectrum to be achieved by control of the dot size during fabrication. The present invention would work well for dye labeled devices, and would be ideal for the narrower spectra presented by quantum dots. The remaining description assumes quantum dots are used, but any fluorophore would fit into this invention. Quantum dots of different colors (different wavelengths) are used to label different chemical or biological species [1]. Depending upon the reaction between the species and quantum dots, quantum dots of different wavelength will be illuminated and observed through a spectrometer. In a further embodiment of the invention, the quantum dots, along with the species, are illuminated in microfabricated chambers or channels that are monolithographically integrated with a planar waveguide based grating element or assembled with such a grating element through hybrid integrating with micro-optics elements. Such an embodiment will preferably cover the fluorescence wavelength detection of quantum dots for chemical, biological and other sensing, and be suitable for fluorescence, absorption and transmission spectroscopic analysis of species including quantum dots.

In another embodiment, a microfabricated planar waveguide based Echelle or arrayed waveguide grating is monolithically or hybrid integrated with microfluidic channels or chambers for specific and easily custom made wavelength detection of species including quantum dots through either absorption or fluorescence or transmission spectroscopic techniques. Spectroscopic devices in accordance with embodiments of the invention may thereby be significantly smaller than known devices. In one particular implementation, a device has a size of approximately 2 cm×2 cm, although the invention is in no way limited to any specific size or range of sizes.

Smaller devices will also reduce device cost, as devices may be fabricated in large numbers through photolithography and microfabrication using standard waveguide materials such as Silica, SiON, Silicon, SOI Silicon, and polymers, for instance.

Figure 2:
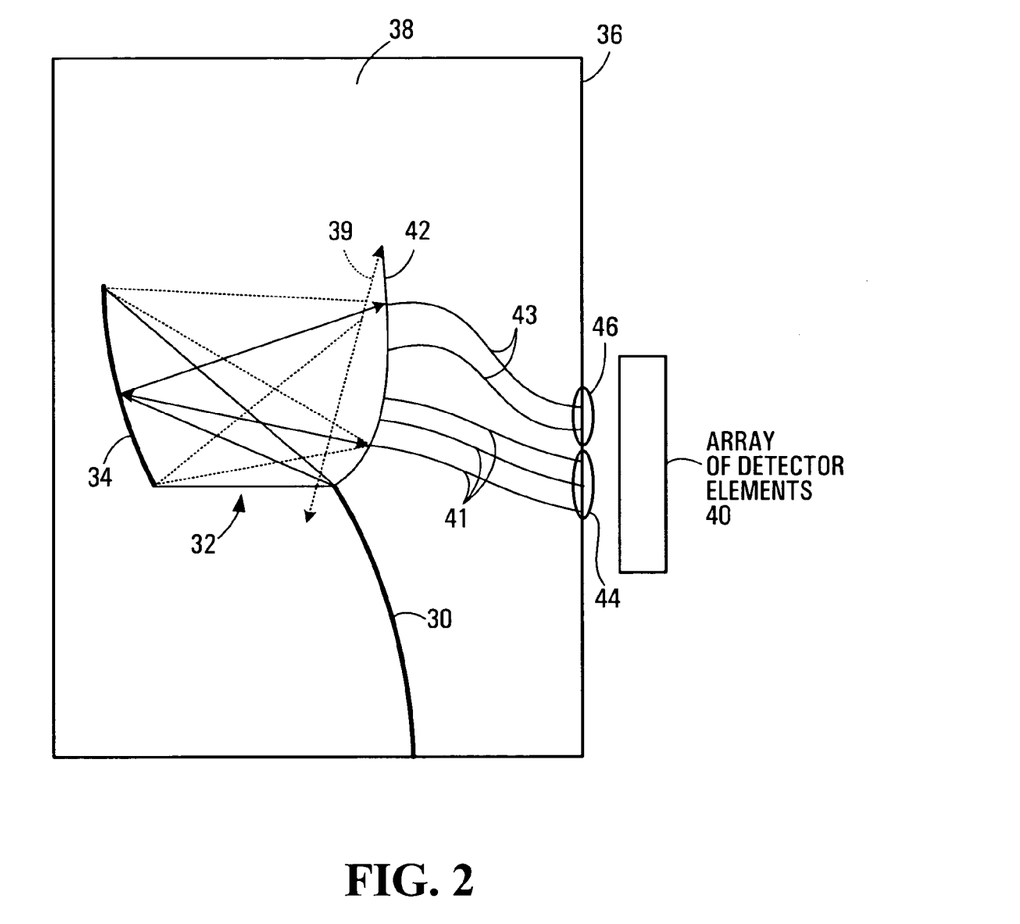
FIG. 2 illustrates a waveguide based spectrometer according to an embodiment of the invention.

FIG. 2 illustrates a waveguide based spectrometer according to an embodiment of the invention, which includes an input waveguide 30, a slab waveguide region 32, a diffractive grating 34, output waveguides 41 and 43, and waveguide termination sections 44 and 46, fabricated on a substrate 38. An array 40 of detector elements is adjacent to, and preferably attached to, an edge 36 of the substrate 38. The slab waveguide region has a core, waveguide region defined by the diffractive grating 34 and curved image surface 42. Preferably, the curved image surface is a Rowland circle having a diameter one half that of the diffractive grating 34. The line 39 represents the dispersion range of wavelength in the case of Rowland configuration and also the straight image line as in the case of flat-field gratings.

It is to be clearly understood that diffractive constructs other than gratings can be employed. Also, while the Rowland circle geometry is preferred, other geometries are contemplated as well, including flat-field gratings which image to a straight line as opposed to a curved image line.

In the optical chip design shown in FIG. 2, the spectral separation is distinguished from the conveyance of light to the detectors 40. In this way, the spectral quality can be improved. Other geometries can alternatively be employed.

An input side of the optical chip of FIG. 2 operates substantially as described above for FIG. 1. However, diffracted light from the diffractive construct 34 is conveyed to two waveguide termination sections 44 and 46 at the edge 36 of the chip by means of optical waveguides 41 and 43. In section 44, the waveguides 41 form a smooth mapping of wavelength to position, whereas in section 46, the waveguides 43 are arranged in such a manner as to bring together widely differing wavelengths. That is, the mapping of wavelengths between the sections 44 and 46, and also the mapping of wavelengths within section 46, are discontinuous with chip edge position. The inter-connecting output waveguides 43 start at the positions on the Rowland circle 42 corresponding to discontinuous ranges of wavelength and end along the edge 36 of the chip in line with detector elements in the array 40. Thus, fewer detector elements are needed to capture the required information from discontinuous wavelengths. In a species-specific detection application of a spectrometer for instance, light is collected only at expected peak wavelengths by properly positioning the waveguides. Detector elements are then provided only for those wavelengths.

The number of detector elements needed to properly capture a spectral line, for instance a signature line of a specimen of interest, is determined by the spectral width of the line under typical measurement conditions, the temperature stability of the size and refractive index of the waveguide spectrometer 34, and the detector signal-to-noise. A typical signature line may require three to ten detector elements. For example, for the detection of fluorophores, one element per dye or quantum-dot color would suffice. Thus for the detection of 4 colours (as expected in DNA sequencing) only 4 elements would suffice. In comparison, standard spectrometers have 256 or more detector elements.

In some embodiments, a spectrometer has overlapping diffraction orders. A large wavelength coverage can be obtained at high resolution by taking advantage of overlapping orders. Some lines of a species could be detected at one diffraction order, while other lines illuminate other detector elements via a different diffraction order.

Figure 3:
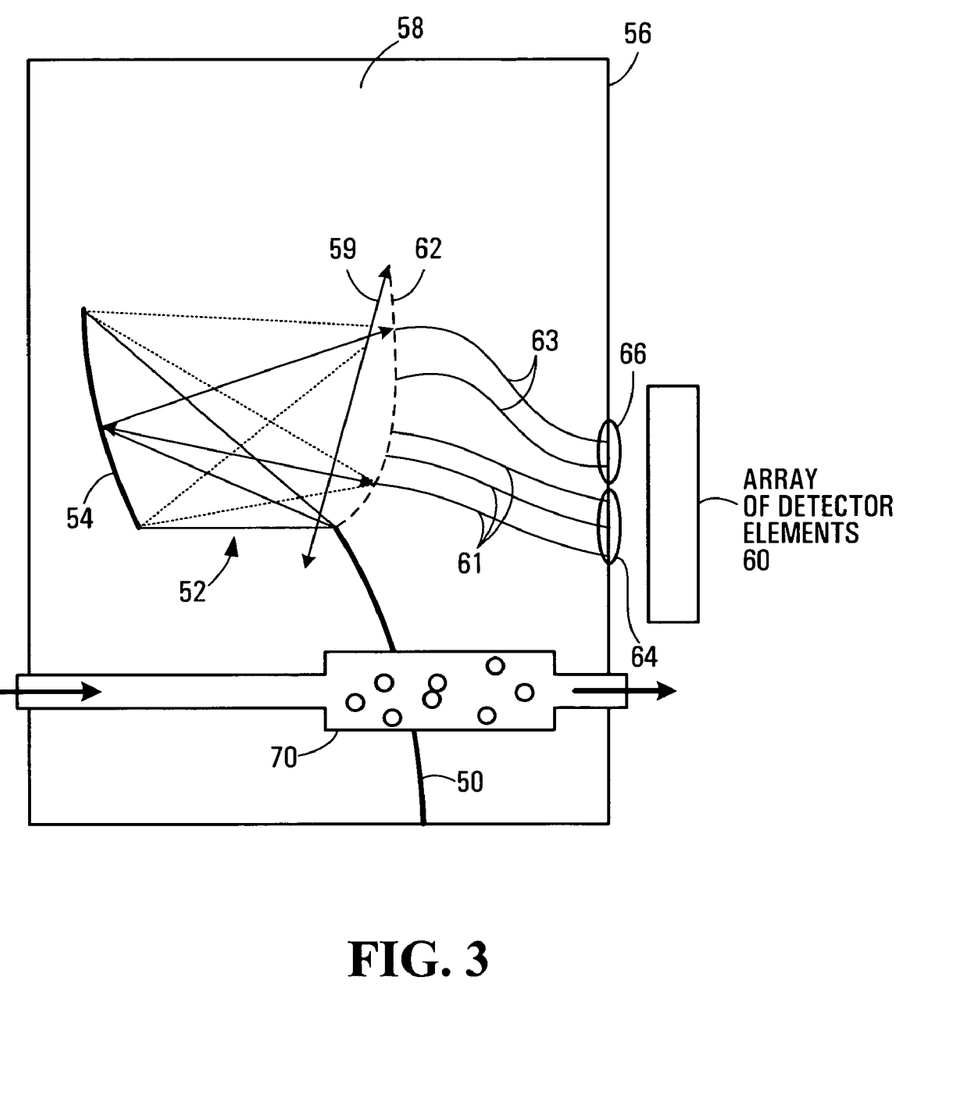
FIG. 3 shows a planar waveguide device with a monolithically integrated microfluidic chamber in an input waveguide path.

According to a preferred embodiment of the invention, a fluid chamber is integrated with a spectrometer. FIG. 3 shows a planar waveguide device with a monolithically integrated microfluidic chamber in an input waveguide path.

The device in FIG. 3 comprises a slab region 52, a diffractive element 54, output waveguides 61 and 63 terminating at sections 64 and 66 along an edge 56 of a substrate 58 proximate an array 60 of detectors. The line 59 represents the dispersion range of wavelength in the case of Rowland configuration and also the straight image line as in the case of flat-field gratings while the 62 represents the curved image line in the case of Rowland configuration.

It will be apparent that the device of FIG. 3 differs from the device of FIG. 2 in that it incorporates a fluid chamber 70, preferably a microfluidic chamber or flow channel integrated into the optical chip substrate 58, in the path of the input waveguide 50. The waveguide 50 thereby comprises a first section for guiding light from an input to the chamber 70 and a second section for guiding light from the chamber 70 to the slab region 52.

A species that is passing through or collected in the chamber 70 is illuminated by input light radiation delivered by the first section of the input waveguide 50, and the wavelength signature of the species is effectively captured. It is not necessary that the input guide 50 be continuous across the channel as drawn in the figure, and it may be more practical in some cases if the input guide were oriented in such a way as to not enter the region of the grating. The species may be chemical, biological, or fluorescent markers like quantum dots, for example. The light is then diffracted from the diffractive construct 54, preferably a grating element, propagates through the respective waveguides 61 and 63, and is detected at the optical detector elements in the array 60. The application wavelength range of quantum dots/florescent markers/fluorescent dyes is typically in the range of about 400-900 nm. As the application wavelength range of standard optical materials like SiO2, SiON, Si, GaAs, InP, etc. cover the visible and NIR (Near Infrared) ranges, the diffraction element 54 can be easily custom designed for quantum dots and other species detection.

Figure 4:
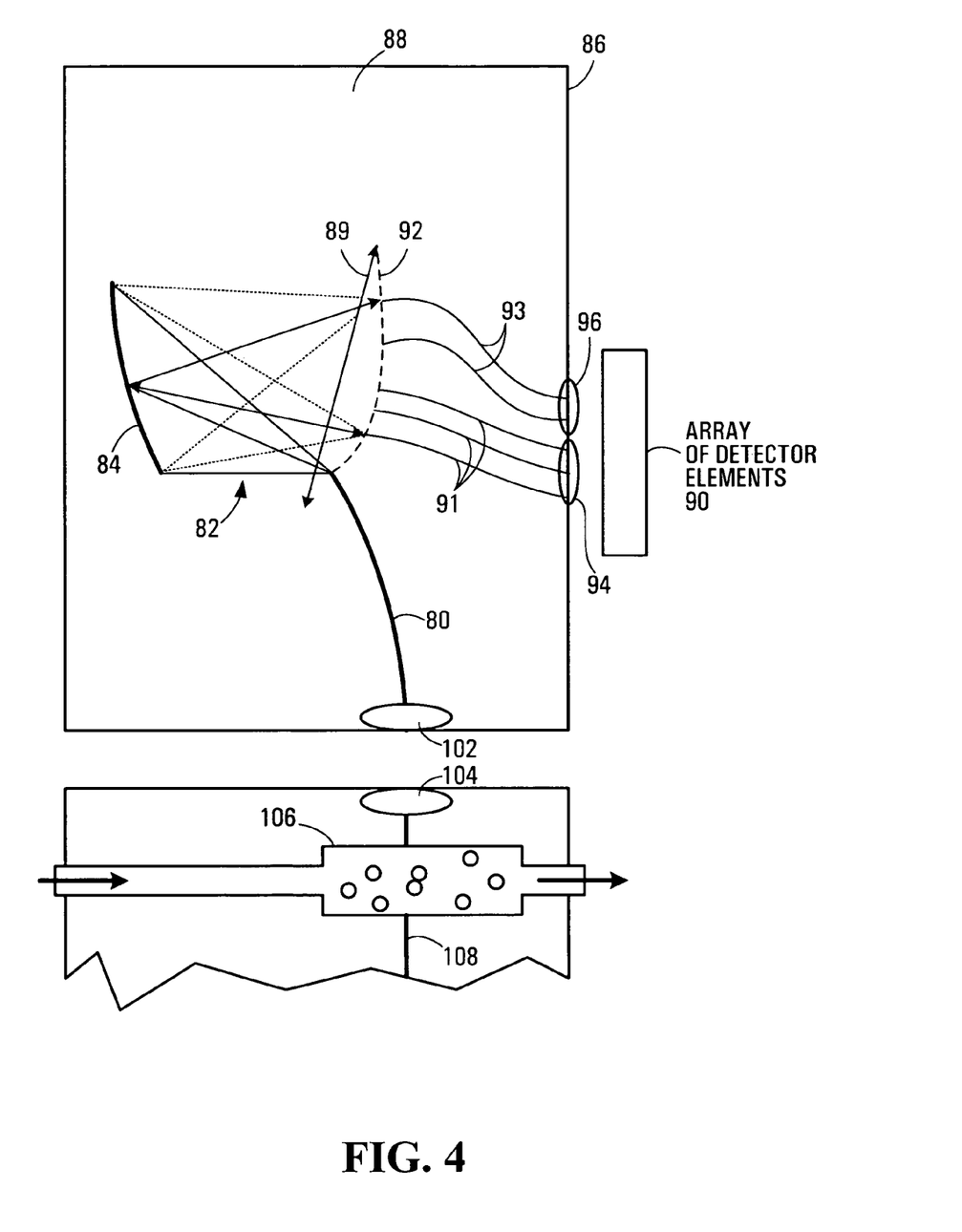
FIG. 4 shows a planar waveguide device with a hybrid integrated microfluidic chamber in an input waveguide path.

In some cases, a microfluidic compartment or chamber could be hybrid integrated with a spectrographic device instead of monolithically integrated as shown in FIG. 3. FIG. 4 shows an example of a spectrometer device with a hybrid integrated microfluidic chamber in an input waveguide path. In the device of FIG. 4, the chamber 106 is coupled to the chip built on the substrate 88 via the optical arrangements 102 and 104. The input waveguide path sections 108 and 80 are also optically coupled through the optical arrangements 102 and 104. The device of FIG. 4, comprising the input waveguide 80, the slab region 82, the diffraction element or grating 84, the output waveguides 91 and 93 terminating at sections 94 and 96 at the edge 86, and the detector element array 90 operates substantially as described above to couple diffracted light from a plurality of positions on the Rowland circle 92, corresponding to different positions on the image line 92, to the sections 94 and 96 adjacent the detectors 90.

Figure 5:
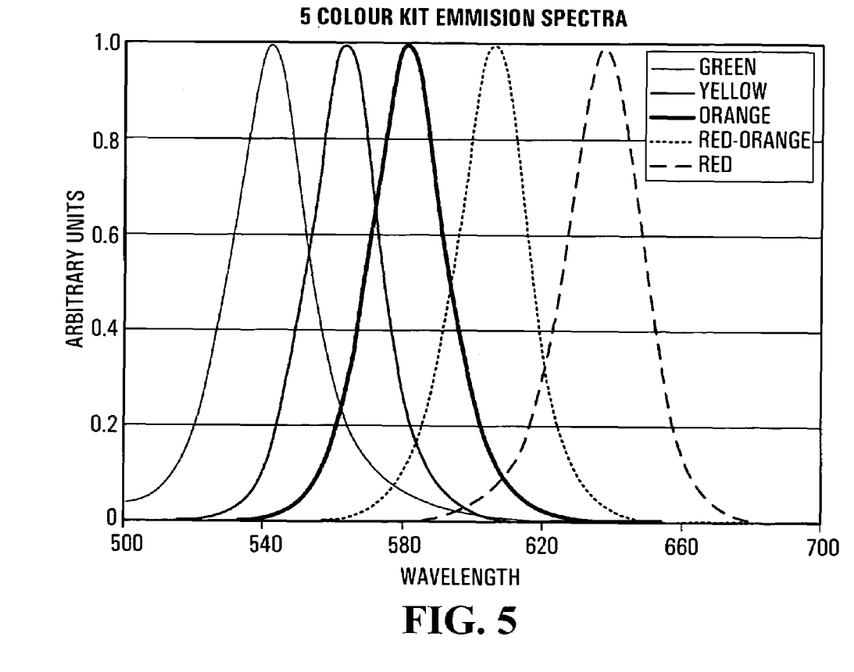
FIG. 5 is an example plot of a fluorescent signature of particular quantum dots.

As an illustrative example, nano quantum dots with peak wavelengths [5] of 535 nm, 560 nm, 585 nm, 610 nm, and 640 nm are presently used for fluorescence detection of many biological species including cancer cells, tissues, etc. The fluorescence spectrum of these quantum dots is shown in FIG. 5. These quantum dots have immense potential for biological detection when integrated with a grating element as described herein. In this case, the grating element preferably has a spectral response the same as or at least substantially similar to that of the fluorescent wavelengths to provide selective diffraction.

An Echelle grating that can be integrated with a quantum dot microfluidics channel/chamber for this particular example has been designed with the following parameters:
Number of input channels/waveguide: 1
Number of output channels/waveguides: 5
Order of the grating: 10
Number of grating facets: 26, with the input and output waveguides being made of silica on silicon. Of course, it is possible to design and fabricate the grating element and waveguides with different materials to optimize performance depending upon requirements of a specific implementation or application.

Figure 6:
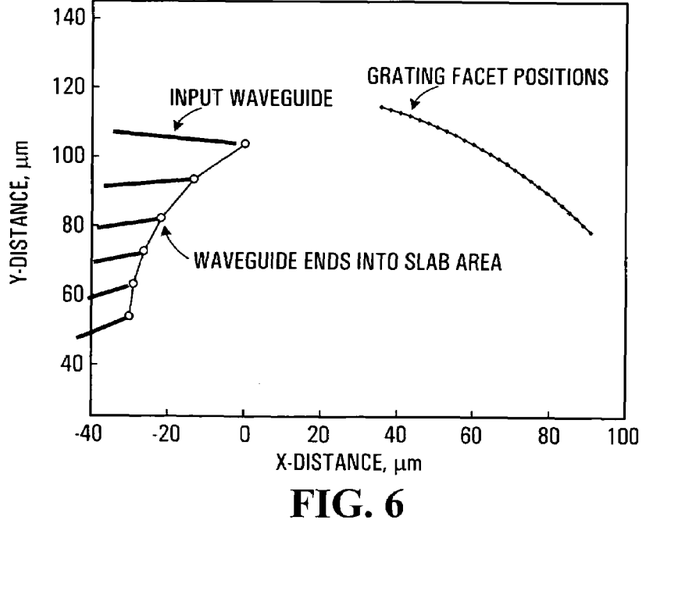
FIG. 6 is an illustrative example of waveguide position and grating facets in a particular embodiment of the invention.
Figure 7:
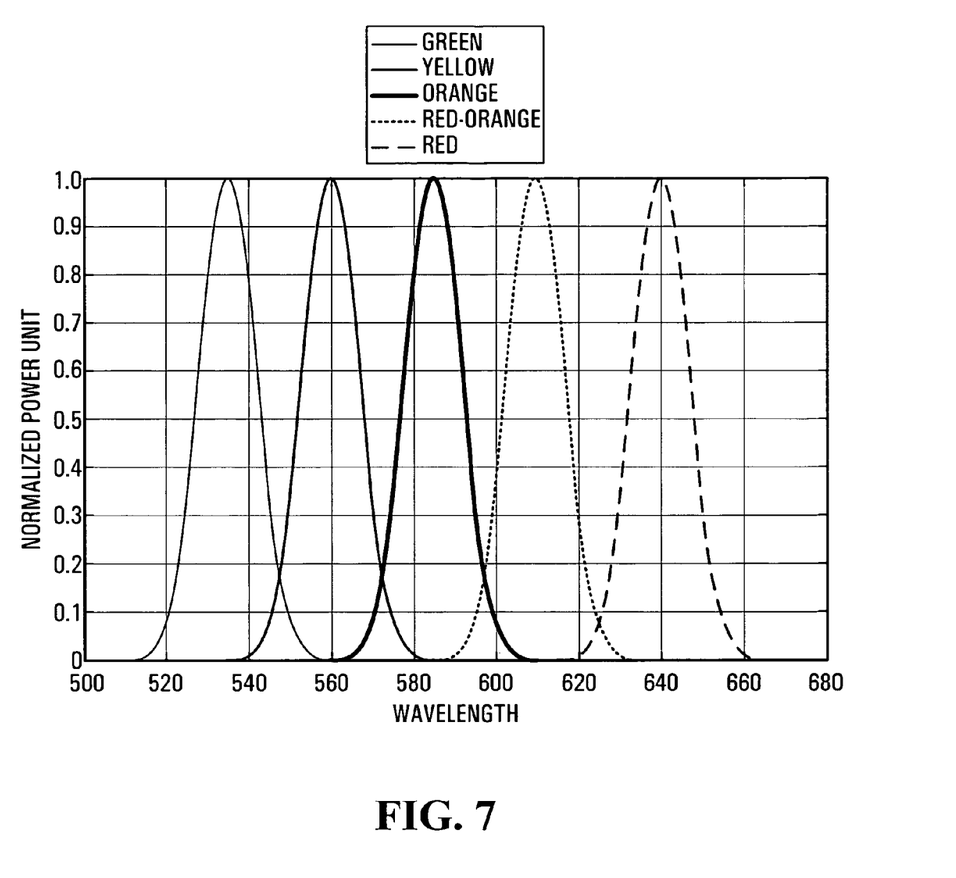
FIG. 7 is an illustrative plot of a spectral response for an example spectrometer device according to an embodiment of the invention.

The waveguide and grating facet locations are shown in FIG. 6, and the spectral response of this spectrometer device is shown in FIG. 7. It can be seen that the peak wavelengths in FIG. 7 are substantially the same as those of quantum dots signature of FIG. 5.

Optical spectrometer devices are thereby provided, for such purposes as chemical/biological spectroscopy, colorimetry, pharmaceutical or petrochemical analysis, and turbidity analysis.

What has been described is merely illustrative of the application of the principles of the invention. Other arrangements and methods can be implemented by those skilled in the art without departing from the spirit and scope of the present invention.

For example, the invention is in no way limited to the particular materials described above. Other suitable materials will be apparent to those skilled in the art.

In addition, it should be appreciated that Echelle gratings and AWG devices are examples of diffractive constructs, and are intended for illustrative purposes.

Although a microfluidic channel has been described primarily in the context of a spectrometer device including output waveguides for mapping desired wavelengths to the output edge of the device, the wavelength mapping and microfluidic channel aspects of the invention are substantially independent and thus need not be implemented together.

REFERENCES

1. Xingyong, Wu., et. al., "Immunofluorescent Labeling of Cancer Marker Her2 and Other Cellular Targets with Semiconductor Quantum Dots', Nature Biotechnology Vol. 21, January 2003, PP. 41-46.
2. Ian Kennedy, "Application of Quantum Dots to Environmental and Cell Biology", NSF Nanoscale Science and Engineering Grantees Conf., Dec. 11-13, 2002.
3. Mark L. Adams, "Microfluidic Integration on Detector Arrays for Absorption and Fluorescence Micro-spectrometers", Sensors and Actuators A, 104, 2003, pp. 25-31.
4. Emilio Gini, et. al., "Polarization Independent InP WDM Multiplexer/Demultiplexer Module", Jrl. of Lightwave Technology, Vol. 16, No. 4, April 1998, pp. 625-630.
5. "High Quality—Production Quantities of Core Semiconductor Nanocrystals for the Nanotechnology Researcher", Evident Technologies, August, 2002.
6. K. A. McGreer, "Flat Field Grating Demultiplexer for WDM", Canadian Journal of Physics, 74, 1996, P. S25-S28.
7. K. A. McGreer, "A Flat Field Broadband Spectrograph Design", IEEE Photonics Technology Letters, Vol. 7, No. 4, April 1995, PP. 397-399.

We claim:

1. A planar waveguide spectrometer apparatus comprising a microfluidic channel or compartment microfabricated integrally with a planar waveguide or hybrid assembled with the planar waveguide and optically coupled thereto, wherein the planar waveguide comprises:
   a thin planar substrate made of a transparent waveguiding optical material having the following features integrally formed thereon;
   a planar multilayer of differing refractive indices to allow guiding of light in a direction disallowing diffusion of light perpendicular to the plane of the layers;
   one or more input waveguides to further guide light radiation transversely from an input edge of the substrate disallowing diffusion of radiation in a direction along the multilayer plane and parallel to the input edge, said input waveguides to guide light a predetermined distance to a termination edge or image line;
   a waveguide-based spectrometer having diffractive elements and slab regions between the input waveguides, the diffractive elements and output waveguides, with an input region coincident to the termination edges of the input waveguides, the diffractive elements being adapted to separate a plurality of input wavelengths into separate focal spots along an image plane of desired curvature perpendicular to the optical guiding multilayer; and
   one or more output waveguides similar to the input waveguides, said output waveguides beginning at the image plane of the spectrometer at positions suitable for capturing radiation at desired wavelengths, and guiding the radiation to an output edge perpendicular to the optical multilayer planes and coincident with an output plane of the termination points of the output waveguides; and
   a detector array placed facing the output edge with detector elements following all or some of the output waveguides at their termination points,
   wherein the microfluidic channel or compartment is microfabricated integrally with the thin planar substrate or hybrid assembled with the thin planar substrate and optically coupled thereto,
   wherein multiple diffraction order from the spectrometer are allowed to illuminate the output waveguides, and unwanted orders are eliminated waveguide-by-waveguide basis by means of lithographically defined scattering from resonant perturbations of the output waveguides or by filters added to the output waveguide paths.

2. The apparatus of claim 1 wherein the planar multilayer comprises at least two layers, with one layer, a guiding layer or core layer, in the midst of all layers having a refractive index exceeding the indices of adjacent layers.

3. The apparatus of claim 2 wherein structures giving transverse definition to the input and output waveguides comprise a pair of walls perpendicular to the plane of the optical layers, cutting through at least the guiding layer, and surrounded on either side by optical material of lower index than that of the guiding layer.

4. The apparatus of claim 2 wherein the spectrometer comprises a planar waveguide at both the input edge and the image plane, said planar waveguide extending to a reflective diffraction grating with grating facets constructed perpendicular to the guiding layer and intersecting the guiding layer.

5. The apparatus of claim 4 wherein the image plane is curved, with radius R, lying on a Rowland circle, and the centers of the grating facets lie in a curved plane of radius twice R.

6. The apparatus of claim 1, wherein an optical fiber is aligned to an input waveguide at the input edge to deliver radiation at a plurality of wavelengths within a predetermined spectral range.

7. The apparatus of claim 1 further comprising an electronic subsystem for collecting signals from the array for processing and correlation, and allowing a processed signal to be interpreted for information about a system being studied using the radiation incident to the input edge of the device.

8. The apparats of claim 1 wherein the desired wavelengths are equispaced for continuous mapping or non-equispaced for the selective mapping of wavelengths.

9. The apparatus of claim 1 optimized for detection of fluorescence from quantum dot fluorescent tags or fluorescent dyes.

10. The apparatus of claim 1 wherein the microfluidic channel or compartment comprises a fluorescence chamber coupled to the planar waveguide via optics.

11. The apparatus of claim 10 wherein the fluorescence chamber is either integrated with the planar waveguide by means of passive alignment therewith or integrated monolithically with the planar waveguide.

12. The apparatus of claim 11, wherein the fluorescence chamber is designed as a standard microfluidies system, employing electro-osmotic flow or pressure induced flow.

13. Use of an apparatus according to claim 1 for DNA sequencing, bio imaging or other applications through wavelength detection of fluorescent markers, fluorescent dyes and quantum dots.

* * * * *

UNITED STATES PATENT AND TRADEMARK OFFICE
CERTIFICATE OF CORRECTION

PATENT NO. : 7,324,195 B2  Page 1 of 1
APPLICATION NO. : 11/031039
DATED : January 29, 2008
INVENTOR(S) : Muthukumaran Packirisamy and Ashok Balakrishnan It is certified that error appears in the above-identified patent and that said Letters Patent is hereby corrected as shown below:

Title page, item [73] under Assignee, "Valorbec Societe Em Commandite" should read --Valorbec Societe En Commandite--;

Column 9, Claim 1, line 45, "eliminated waveguide" should read --eliminated on a waveguide--;

Column 10, Claim 8, line 29, "apparats" should read --apparatus--;

Column 10, Claim 8, line 31, "for the selective" should read --for selective--; and Column 10, Claim 12, line 44, "microfluidies" should read --microfluidics--.

Signed and Sealed this

Seventeenth Day of June, 2008

JON W. DUDAS
*Director of the United States Patent and Trademark Office*